United States Patent [19]

Znaiden et al.

[11] Patent Number: 6,159,487

[45] Date of Patent: Dec. 12, 2000

[54] MOISTENED COSMETIC EYE TREATMENT PADS

[75] Inventors: Alexander Paul Znaiden, Trumbull; Brian Andrew Crotty, Branford, both of Conn.; Paul Dennis Gural, South Huntington, N.Y.

[73] Assignee: Chesebrough-Pond's USA Co., division of Conopco, Inc., Greenwich, Conn.

[21] Appl. No.: 09/071,661

[22] Filed: May 1, 1998

Related U.S. Application Data

[60] Provisional application No. 60/079,146, Mar. 24, 1998.

[51] Int. Cl.[7] ............................................. A01N 25/34
[52] U.S. Cl. ..................... 424/402; 424/400; 424/443; 424/444; 424/445; 424/446; 424/447; 424/448; 424/449
[58] Field of Search ..................... 424/400, 402, 424/443–449

[56] References Cited

U.S. PATENT DOCUMENTS

| | | | |
|---|---|---|---|
| 2,983,369 | 5/1961 | Rogovin | 206/56 |
| 4,891,227 | 1/1990 | Thaman et al. | 424/443 |
| 4,979,811 | 12/1990 | Boyer | |
| 5,024,325 | 6/1991 | Gundlach | |
| 5,302,446 | 4/1994 | Horn | 428/286 |
| 5,620,694 | 4/1997 | Girardot | 424/402 |
| 5,888,524 | 3/1999 | Cole | 424/402 |

FOREIGN PATENT DOCUMENTS

| | | |
|---|---|---|
| 0 531 096 | 3/1993 | European Pat. Off. |
| 35 24 392 | 7/1985 | Germany |
| 621 932 | 2/1977 | Switzerland |
| 2 222 526 | 3/1990 | United Kingdom |

Primary Examiner—S. Mark Clardy
Assistant Examiner—Kathryne E. Shelborne
Attorney, Agent, or Firm—Milton L. Honig

[57] ABSTRACT

A cosmetic product, particularly for the eye, is provided which includes a container, an absorbent pad with printing on at least one major surface, and a fluid cosmetic composition, the pad and composition being held within the container. The cosmetic composition is primarily water, especially amounts of water in excess of 90%. Most preferred as a substrate for the pad is a non-woven polyester. A cucumber slice design is the most preferred print on the pad. A method is also provided which reduces puffiness, soothes the eye and lessens dark circles around the eye. This method involves applying the aforementioned cosmetic composition via the pad onto the eye and its surrounding area.

13 Claims, 1 Drawing Sheet

MOISTENED COSMETIC EYE TREATMENT FADS

This is a completion of Provisional Application Serial No. 60/079,146 filed Mar. 24, 1998.

BACKGROUND OF THE INVENTION

1. Field of the Invention

The invention concerns cosmetic pads for soothing tired, stressed-out eyes.

2. The Related Art

Exhausting days, late nights. These can exact a toll, especially on a person's eyes. Commercially there are available a host of eye treatment products. Creams and lotions are topically applied on surrounding skin areas to tame dark circles or puffiness.

Placement of cucumber slices over the eyes has become quite popular as part of a home beauty regime. Salons and health spas are known to place cucumber slices over the eyes while applying a mud facial. Sliced cucumber treatment is not only a cosmetic but an existential experience. It renews both body and spirit.

Cucumbers are not always in season. Vegetable quality is variable. Refrigeration is necessary. A cosmetic approach is not hindered by such problems. Indeed, science can sometimes improve over nature. It would be highly desirable to have a vegetable slice substitute, fully interchangeable with the real article yet readily storable, of uniform quality and perhaps even more effective than the original.

Accordingly, it is an object of the present invention to provide a pre-moistened eye pad designed as a vegetable slice substitute for use as a soothing eye treatment.

Another object of the present invention is to provide a pre-moistened pad designed to rest on top of the eyes delivering a cooling sensation and natural aroma of freshly cut cucumber or other vegetable slice.

Still a further object of the present invention is to provide eye pads pre-moistened with an aqueous fluid that is non-irritant and microbially safe.

SUMMARY OF THE INVENTION

A cosmetic product is provided, especially for placement over the eyes which includes:

(i) a sealable container;

(ii) at least one absorbent pad with printing on at least one major surface thereof, the pad being enclosed within the container; and (iii) a fluid cosmetic composition within the container and at least partially absorbed onto the absorbent pad.

Additionally, there is provided a method for treating eye areas to reduce or lessen puffiness, dark circles, redness and combinations thereof, the method including applying over the eyes a pad with printing thereon and impregnated with a cosmetic composition.

DETAILED DESCRIPTION OF THE DRAWING

Figure 1:
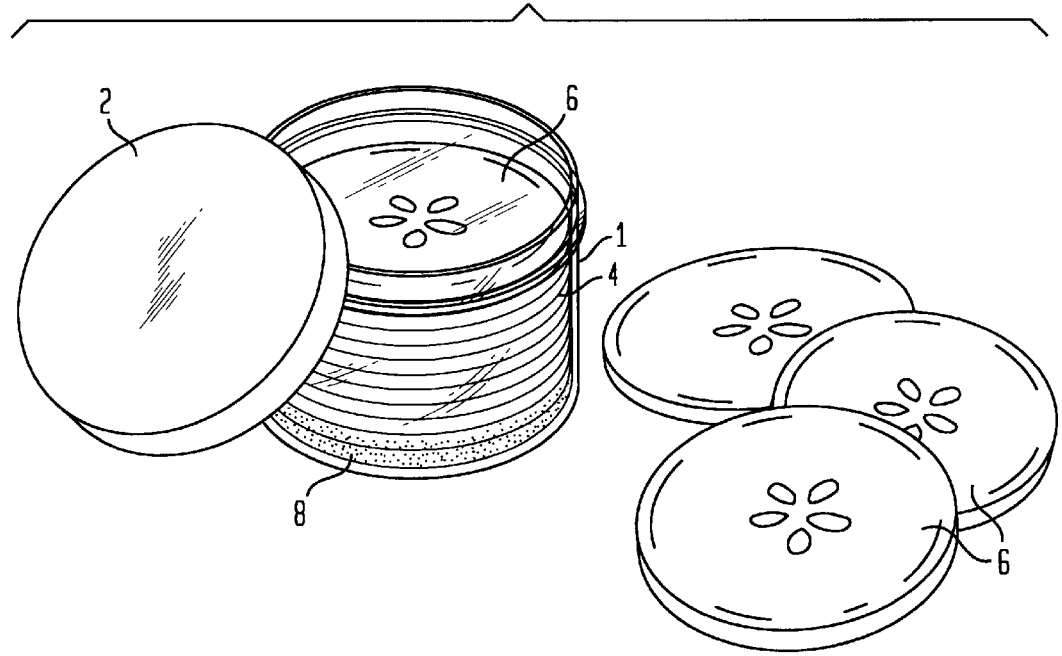
Figure 2:
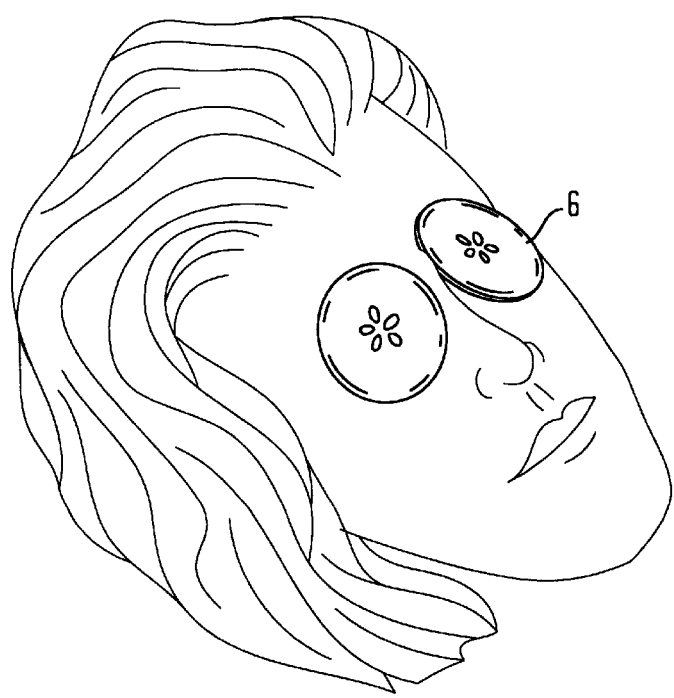

Further objects, features and advantages of the present invention will become more evident from the following drawing in which:

FIG. 1 is a perspective view of a jar with cap removed, containing printed cucumber slice pads stacked within the jar and three pads being arranged outside for better viewing; and FIG. 2 is a woman's face with eyes being soothed by a pair of cucumber slice printed pads.

DETAILED DESCRIPTION OF THE INVENTION

FIG. 1 illustrates the product of this invention. A jar 1 fitted with a cover 2 is employed to store a stack 4 of pads 6. A puddle of an aqueous cosmetic composition 8 is held within jar 1.

Anywhere from 5 to 50 pads, preferably 10 to 30 pads are stacked in a container. Preferably the container is a rigid jar, and preferably of clear glass or plastic to allow viewing of its contents. Alternatively, the container can be a sealed pouch, particularly a laminated foil pouch. The advantage of pouches is that they are of travel size. One or two pads can economically be packaged therein.

A user selects one or two of the cucumber slice printed pads and places them respectively over the eye area. FIG. 2 illustrates application of these pads. Among the benefits of application include a reduction in puffiness, soothing the eye area, lessening of dark circles around the eye and imparting a general relaxation effect with cooling sensation and the natural aroma of freshly cut vegetables. Maximum benefit can be achieved by storing the pads at refrigerator temperature (less than 25° C.). Application of the refrigerated pads increases the soothing effects.

Pads according to the present invention may be constituted of any material including natural and synthetic fibers. Thus, there may be employed as natural fibers wood pulp, cotton and wool. Synthetic fibers suitable for the invention include rayon, polyethylene, polypropylene, polyester and mixtures of these synthetics as well as mixtures of synthetic with natural fibers. The pads may be woven or non-woven. Even though many of the aforementioned substrates may be employed, printability, texture and other properties of most of these materials may not be optimum for purposes of this invention. The most suitable substrate is a non-woven polyester. This material can easily be printed but yet is not as stiff as rayon, polyethylene or polypropylene. The substrates may be single or multiple ply. A single ply polyester is preferred.

Cosmetic compositions of the present invention will contain from 50 to 100% water, preferably from 80 to 99.9%, optimally from 90 to 98% water.

Compositions of the present invention may also contain polyhydric alcohols. Typical of these alcohols are glycerol, propylene glycol, ethylene glycol, dipropylene glycol, polypropylene glycol, polyethylene glycol, butylene glycol, sorbitol, hydroxypropyl sorbitol, hexylene glycol, ethoxylated glycerol, propoxylated glycerol and mixtures thereof. Butylene glycol is preferred. Amounts of the polyhydric alcohol may range from 0.1 to 45%, preferably from 0.5 to 30%, optimally from 1 to 10% by weight of the composition.

Natural botanical ingredients may be included in cosmetic compositions of the present invention. These substances include plant purees, extracts and vitamins. Amounts of these substances may range from 0.00001 to 10%, preferably from 0.0001 to 2%, optimally from 0.001 to 1% by weight of the total composition.

Suitable vitamins are Vitamin A, Vitamin B, Vitamin C and Vitamin E as well as their derivatives.

Typical plants from which extracts and other derivatives can be obtained or use in the present invention include the following:

| | |
|---|---|
| Wormwood | (Artemisia Absinthium) |
| Acacia | (Robinia pseudoacacia) |
| Agrimony | (Agrimonia Eupatoria) |
| Amryllis | (Amaryllis) |
| Colombine | (Aquilegia vulgaris) |
| Anemone | (Anemone spp) |
| Mugwort | (Artemisia vulgaris) |
| Arnica | (Arnica montana) |
| Sweet Woodruff | (Asperula odorata) |
| Hawthorn | (Crotaegus oxyacantha) |
| Azalea | (Azalea spp) |
| Balsamine | (Impatiens spp) |
| Begonia | (Begonia spp) |
| Bougainvillea | (Bougainvillea spp) |
| Waterelder | (Viburnum opulus) |
| Cornflower | (Centaurea Cyanus) |
| Mullein | (Verbascum spp) |
| Common heather | (Calluna vulgaris) |
| Barbary fig | (Opuntia vulgaris) |
| Camellia | (Camellia japonica) |
| Chamomile | (Anthemis nobilis) |
| Campanula | (Campanula spp) |
| Large Indian Cress | (Tropeolum majus) |
| Safflower | (Carthamus tinctorius) |
| | (Catalpa bignomioides) |
| Star thistle | (Centaurea calcitrapa) |
| Rough Cherry | (Prunus cerasus) |
| Honeysuckle | (Lonicera spp) |
| Daisy | (Chrysanthemum leucoanthemum) |
| Travelle's Joy | (Clematis vitalba) |
| Quince | (Cydonia vulgaris) |
| Red poppy | (Papaver Rhoeas) |
| Colchicum or Meadow Saffron | (Colchicum automnale saffron) |
| Cornel tree (or dogwood) | (Cornus spp) |
| Crocus | (Crocus spp) |
| Cyclamen | (Cyclamen spp) |
| Dahlia | (Dahlia variabilis) |
| Field larkspur | (Delphinium consolida) |
| Dulcamara | (Solanum Dulcamara) |
| | (Leontopodium Alpinum) |
| Dog rose | (Rosa canina) |
| Fumitory | (Fumaria officinalis) |
| Broom | (Cytisus scoparius) |
| Gentian | (Gentiana spp) |
| Geranium | (Geranium spp) |
| Wallflower | (Cheirantus cheiri) |
| Sword-lily | (Gladialus spp) |
| Marsh Mallow | (Althaea officinalis) |
| | (Gypsophila spp) |
| Roselle | (Hibiscus spp) |
| Hydrangea | (Hydrangea spp) |
| Hops | (Humulus lupulus) |
| Live ever | (Helicrysum arenarium) |
| Garden balsam | (Impatiens spp) |
| Orrice | (Iris spp) |
| Hyacinthe | (Hyacynthus spp) |
| Jasmine | (Jasminum spp) |
| Jonquil | (Narcissus jonquilla) |
| Oleander | (Nerium oleander) |
| Lavender | (Lavandule officinalis) |
| | (Lavatera spp) |
| Lilac | (Syringa vulgaris) |
| White lily | (Lilium candidum) |
| Bindweed | (Conedvalus spp) |
| Lupin | (Lupinus albus) |
| Magnolia | (Magnolia spp) |
| Daisy | (Chrysanthemum leucanthemum) |
| Horsechestnut | (Aesculus Hippocastanum) |
| Wild chamomile | (Matricaria chamomilla) |
| Mallow | (Malva spp) |
| Melilot | (Melilotus officinalis) |
| Mint | (Mentha spp) |
| St John's Wort | (Hypericum perforatum) |
| Mimosa | (Mimosa spp) |
| Lion's mouth | (Antirrhinum majus) |
| Mugget | (Convallaria maialis) |
| Myosotis | (Myosotis spp) |
| Daffodil | (Narcissus spp) |
| White water Lily | (Nymphaea alba) |
| Gilower | (Dianthus caryophyllus) |
| Marigold | (Tagetes spp) |
| Sweet orange Tree | (Citrus Aurantium) |
| Orchid | |
| Daisy | (Bellis perennis) |
| Passion flower | (Passiflora spp) |
| Peach-tree | (Prunus persica) |
| Pelargonium | (Pelargonium spp) |
| Pansy | (Viola spp) |
| Snowdrop | (Galanthus nivalis) |
| Periwinkle | (Vinca spp) |
| Petunia | (Petunia spp) |
| Phlox | (Phlox spp) |
| Field larkspur | (Delphinium consolida) |
| Garden peony | (Paeonia officinalis) |
| Sweat pea | (Lathyrus odorantes) |
| | (Polygonum spp) |
| Apple tree | (Pirus malus) |
| Primrose | (Primula spp) |
| Silver weed | (Potentille Anserina) |
| Plum-tree | (Prunus domestica) |
| Pyrethum | (Chrysanthemum cineriaefolium) |
| Meadow Sweet | (Spiraea Ulmaria) |
| Buttercup | (Ranuncukus spp) |
| Rhododendron | (Rhododendron ferrugineum) |
| Rose mary | (Rosmarinus officinalis) |
| French Rose | (Rose gallica) |
| Saffron | (Crocus sativus) |
| Grass polly | (Lythrum salicaria) |
| Bloodroot | (Sanguinaria canadiensis) |
| Soapwort | (Saponaria officinalis) |
| Sage | (Salvia officinalis) |
| Willow | (Salix alba) |
| Devil's bit scabiou | (Scabiosa Succisa) |
| Syringa | (Philadelphus coronarius) |
| Serpollet | (Thymus serpylum) |
| | (Sophora japonica) |
| Corme | (Sorbus domestica) |
| Marigold | (Calandula officinalis) |
| Spiraea | (Spiraea spp) |
| Elder | (Sambucus nigra) |
| Tamarisk | (Tamaris gallica) |
| Tansy | (Tanatecum vulgare) |
| Garden thyme | (Thymus vulgaris) |
| Lime | (Tilia spp) |
| Clover | (Trifolium spp) |
| Tulip | (Tulipa spp) |
| Coltsfoot | (Tussilago larfara) |
| Speedwell | (Veronica officinalis) |
| Common vervain | (Verbena officinalis) |
| Violet | (Viola spp) |
| Yucca | (Yuccas spp) |

When the pads are printed and designated as "cucumber slices", compositions of this invention will contain a cucumber puree, cucumber extract or other derivative of natural cucumbers. It is to be understood that this invention is not limited to "cucumber slices". Printing and designation of the pads may be to any fruit, vegetable or plant substance. There may even be instances where the pads are printed but are not intended to resemble or refer to any vegetable/fruit/plant. Instead, words or logos may be printed therein.

Small amounts of emulsifiers may also be included in compositions according to the present invention. Emulsifiers may be selected from anionic, nonionic, cationic and amphoteric actives. Illustrative nonionic emulsifiers are those with a $C_{10}$–$C_{20}$ fatty alcohol or acid hydrophobe condensed with from about 2 to about 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic actives. Particularly preferred are alkoxylated triglycerides, especially castor oil condensed with 40 to 100 moles ethylene oxide.

Preferred anionic emulsifiers include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates and combinations thereof.

Amounts of the emulsifier may range from 0.01 to 10%, preferably from 0.1 to 1%, optimally from 0.15 to 0.5% by weight of the total composition.

Aqueous systems ordinarily require preservatives to prevent growth of potentially harmful microorganisms. A variety of preservatives are known to the art. These include alkyl esters of para-hydroxybenzoic acid, hydantoin derivatives, propionate salts, quaternary ammonium compounds, phenoxyethanol, methyl paraben, propyl paraben, butyl paraben, imidazolidinyl urea, sodium dehydro acetate, benzyl alcohol and mixtures thereof. The type and amount of the preservative(s) is selected for this invention based upon lowest irritancy against the eye and most effective antimicrobial protection. Most preferred for purposes of this invention is sodium hydroxymethylglycinate commercially available as Suttocide A® from the Sutton Laboratories, Inc. Particularly preferred is a combination of Suttocide A® and methyl paraben/ethyl paraben.

Amounts of the preservative may range from 0.01 to 3%, preferably from 0.1 to 1%, optimally from 0.2 to 0.5% by weight of the total composition.

A primary aspect of the present is that the pads are printed with one or more inks. These may be black or colored. Particularly preferred are combinations of yellow and blue (or green). Printing may either be on one major surface or both of the major surfaces of the pad.

The principal processes for printing from a pre-press image include lithography, gravure, flexography, letterpress and screen processes. Newer technologies also include thermal printing, electrophotography and inkjet printing. These are all well described in the Encyclopedia of Chemical Technology, Vol. 20 (4th Edition), pages 62–128, Wiley-Interscience 1996. The preferred form of printing is gravure. Other methods of printing may be employed but gravure is the optimum mode.

The gravure printing process, sometimes called intaglio or rotogravure, utilizes a recessed image plate cylinder to transfer the image to the substrate. The plate cylinder can be either chemically or mechanically etched or engraved to generate the image cells. The volume of these cells determines the darkness or lightness of the image. If an area is darker, the cells are larger; if the area is lighter, the cells are smaller.

In gravure, all elements within the image are screened. This is in contrast to flexographic and lithographic plates, which can contain true solids as well as halftones.

The gravure printing process is based around an inking system that is extremely simple, giving the process a high degree of consistency, particularly with regard to color printing. This consistency is difficult to match using other printing techniques. The system utilizes a liquid ink that has traditionally been solvent-based, although environmental pressures have resulted also in the development of aqueous-based inks.

The gravure cylinder sits in the ink fountain and is squeegeed off with a doctor blade as it rotates. The impression cylinder is covered with a resilient rubber composition, which presses the pad substrate into contact with the ink in the tiny cells of the printing surface. The image is thus transferred directly from the gravure cylinder to the substrate. Frequently an electrostatic assist is used to help the ink transfer from the gravure cylinder to the substrate. Gravure inks are comprised of pigment, resin binder, and, most frequently, a volatile solvent. The ink is quite fluid and dries entirely by evaporation. In multicolor printing, where two or more gravure units operate in tandem, each color dries before the next is printed. This is seen as a particular advantage for gravure over, for example, offset, where the placing of wet ink on wet ink can lead to inferior print quality.

The following examples will more fully illustrate embodiments of this invention. All parts, percentages and proportions referred to herein and in the appended claims are by weight unless otherwise indicated.

EXAMPLE 1

A roll of non-woven polyester fabric under the trademark Sontara® from Dupont was placed under tension between a set of rollers. The web of polyester was then printed-from gravure plates with yellow and blue inks to simulate a cucumber slice cross-section. Thereafter the printed web was delivered to a station where a cutting machine cut in register the cucumber slice simulated print pattern from the web. Twenty-five pads were placed in a screw cap jar. An aqueous composition of the formula listed in Table I was added to the jar, ensuring a saturated atmosphere throughout the jar.

TABLE I

| INGREDIENT | WEIGHT % |
|---|---|
| Cucumber Puree | 1.750 |
| Cucumber Distillate | 1.000 |
| Chamomile Extract* | 0.250 |
| Cornflower Extract CE* | 0.250 |
| Methyl Paraben | 0.200 |
| PEG-40 Castor OiL | 0.150 |
| Aloe Concentrate | 0.100 |
| Green Tea Extract* | 0.100 |
| Rose Hips Extract* | 0.100 |
| Suttocide A ® | 0.100 |
| Ethyl Paraben | 0.050 |
| Disodium EDTA | 0.050 |
| Citrus Bioflavonoids | 0.005 |
| Bisabolol | 0.005 |
| Vitamin E Acetate | 0.001 |
| Deionized Water | balance |

*Extracts are dissolved in water/butylene glycol.

EXAMPLE 2

Another aqueous composition for use with the pads and process of Example 1 is reported in Table II.

TABLE II

| INGREDIENT | WEIGHT % |
|---|---|
| Carrott Puree | 1.750 |
| Carrott Distillate | 1.000 |
| Tea Tree Oil | 0.250 |
| Tween 80 ® | 0.250 |
| Methyl Paraben | 0.200 |
| Glycerin | 0.150 |
| Aloe Concentrate | 0.100 |

TABLE II-continued

| INGREDIENT | WEIGHT % |
|---|---|
| Green Tea Extract* | 0.100 |
| Rose Hips Extract* | 0.100 |
| Suttocide A ® | 0.100 |
| Ethyl Paraben | 0.050 |
| Disodium EDTA | 0.050 |
| Citrus Bioflavonaids | 0.005 |
| Bisabolol | 0.005 |
| Vitamin E Acetate | 0.001 |
| Deionized Water | balance |

*Extracts are dissolved in water/butylene glycol.

EXAMPLE 3

Another aqueous composition for use with the pads and process of Example 1 is reported in Table III.

TABLE III

| INGREDIENT | WEIGHT % |
|---|---|
| Kiwi Fruit Puree | 1.750 |
| Kiwi Fruit Distillate | 1.000 |
| Green Tea Extract | 0.250 |
| Cornflower Extract CE* | 0.250 |
| Methyl Paraben | 0.200 |
| Magnesium Ascorbyl Phosphate | 0.150 |
| Aloe Concentrate | 0.100 |
| Green Tea Extract* | 0.100 |
| Rose Hips Extract* | 0.100 |
| Suttocide A ® | 0.100 |
| Ethyl Paraben | 0.050 |
| Disodium EDTA | 0.050 |
| Citrus Bioflavonoids | 0.005 |
| Potassium Glycyrrhizate | 0.005 |

TABLE III-continued

| INGREDIENT | WEIGHT % |
|---|---|
| Vitamin E Acetate | 0.001 |
| Deionized Water | balance |

*Extracts are dissolved in water/butylene glycol.

EXAMPLE 4

Still another aqueous composition for use with the pads and process of Example 1 is reported in Table IV.

TABLE IV

| INGREDIENT | WEIGHT % |
|---|---|
| Orange Puree | 1.750 |
| Orange Distillate | 1.000 |
| Vitamin C | 0.250 |
| Cornflower Extract CE* | 0.250 |
| Methyl Paraben | 0.200 |
| PEG-40 Castor Oil | 0.150 |
| Aloe Concentrate | 0.100 |
| Green Tea Extract* | 0.100 |
| Rose Hips Extract* | 0.100 |
| Suttocide A ® | 0.100 |
| Ethyl Paraben | 0.050 |
| Disodium EDTA | 0.050 |
| Citrus Bioflavonoids | 0.005 |
| Bisabolol | 0.005 |
| Vitamin E Acetate | 0.001 |
| Deionized Water | balance |

*Extracts are dissolved in water/butylene glycol.

EXAMPLE 5

A series of different preservatives were evaluated in the composition of Example 1. These were tested to determine their irritancy toward the eye. Table V lists the tested preservatives and their eye irritation and microbiological properties.

TABLE V

| TEST NO. | PRESERVATIVE SYSTEM | WEIGHT % | EYE STING INTENSITY | SKIN STING INTENSITY | MICROBIOLOGICAL RESPONSE |
|---|---|---|---|---|---|
| 1 | Methyl Poroben | 0.2 | | | |
| | Propyl Paroben | 0.05 | + | ++++ | Adequate |
| | Germall 115 ® | 0.2 | | | |
| 2 | Methyl Paraben | 0.2 | No Sting | + | Not Adequate |
| | Propyl Paraben | 0.05 | | | |
| 3 | Methyl Paraben | 0.2 | +++ | Not Tested | Not Adequate |
| | Propyl Paraben | 0.05 | | | |
| | K Sorbote | 0.1 | | | |
| 4 | Methyl Paraben | 0.2 | ++++ | Not Tested | Not Adequate |
| | Propyl Paraben | 0.05 | | | |
| | Phenoxyethonol | 0.4 | | | |
| 5 | Methyl Paraben | 0.2 | + | ++++ | Adequate |
| | Ethyt Paraben | 0.05 | | | |
| | Germall 115 ® | 0.2 | | | |
| 6 | Methyl Paraben | 0.2 | + | +++ | Adequate |
| | Ethyl Paraben | 0.05 | | | |
| | Germall 115 ® | 0.1 | | | |
| 7 | Methyl Paraben | 0.2 | + | +++ | Adequate |
| | Ethyl Paraben | 0.05 | | | |
| | Germall 115 ® | 0.15 | | | |
| 8 | Methyl Paraben | 0.2 | ++++ | Not Tested | Not Tested |
| | Propyl Paraben | 0.05 | | | |
| | Glydant ® | 0.1 | | | |
| 9 | Methyl Paraben | 0.2 | ++++ | Not Tested | Not Tested |
| | Propyl Paraben | 0.05 | | | |
| | Glydant Plus ® | 0.1 | | | |
| 10 | Methyl Paraben | 0.2 | Not Tested | ++++ | Not Adequate |
| | Propyl Paraben | 0.05 | | | |

TABLE V-continued

| TEST NO. | PRESERVATIVE SYSTEM | WEIGHT % | EYE STING INTENSITY | SKIN STING INTENSITY | MICROBIOLOGICAL RESPONSE |
|---|---|---|---|---|---|
| 11 | Benzyl Alcohol | 0.1 | Not Tested | ++++ | Adequate |
|    | Methyl Paraben | 0.2 | | | |
|    | Propyl Paraben | 0.05 | | | |
|    | Benzyl Alcohol | 0.05 | | | |
|    | Germall 115 ® | 0.05 | | | |
| 12 | Methyl Paraben | 0.2 | No Sting | + | Not Complete |
|    | Ethyl Paraben | 0.05 | | | |
|    | Suttocide A ® | 0.1 | | | |
| 13 | Methyl Paraben | 0.2 | No Sting | ++ | Not Complete |
|    | Ethyl Paraben | 0.05 | | | |
|    | Suttocide A ® | 0.1 | | | |
|    | Dowicil 200 ® | 0.15 | | | |
| 14 | Methyl Paraben | 0.2 | No Sting | + | Not Complete |
|    | Ethyl Paraben | 0.05 | | | |
|    | Suttocide A ® | 0.1 | | | |
|    | Dowicil 200 ® | 0.1 | | | |
| 15 | Methyl Paraben | 0.2 | No Sting | + | Not Complete |
|    | Ethyl Paraben | 0.05 | | | |
|    | Suttocide A ® | 0.1 | | | |
|    | Merguard 1190 ® | 0.3 | | | |
| 16 | Methyl Paraben | 0.2 | No Sting | + | Not Complete |
|    | Ethyl Paraben | 0.05 | | | |
|    | Suttocide A ® | 0.1 | | | |
|    | Merguard 1190 ® | 0.2 | | | |
| 17 | Methyl Paraben | 0.2 | No Sting | Not Complete | Not Complete |
|    | Ethyl Paraben | 0.05 | | | |
|    | Suttocide A ® | 0.1 | | | |
|    | Merguard ® | 0.3 | | | |
|    | Germall 115 ® | 0.025 | | | |
| 18 | Methyl Paraben | 0.2 | No Sting | Not Complete | Not Complete |
|    | Ethyl Paraben | 0.05 | | | |
|    | Suttocide A ® | 0.1 | | | |
|    | Merguard 1190 ® | 0.1 | | | |
|    | Germall 115 ® | 0.025 | | | |
| 19 | Methyl Paraben | 0.2 | No Sting | + | Not Complete |
|    | Ethyl Paraben | 0.05 | | | |
|    | Suttocide A ® | 0.1 | | | |
|    | Merguard 1190 ® | 0.3 | | | |
|    | Dowicil 200 ® | 0.05 | | | |

Increased number of (+) indicates increased sting intensity.
Glydant ® has CTFA name of DMDM Hydantoin; chemically known as 1,3-Dimethylol-5,5-Dimethyl Hydantoin
Dowicil 200 has CTFA name of Quarternium 15; chemically known as N-(3-Chloroallyl) Hexaminium Chloride
Suttocide A has CTFA name of Sodium Hydroxymethylglycinate
Germal 115 has CTFA name of Imidazolidinyl Urea
Glydant Plus ® is a mixture Iodopropynyl Butylcarbamate and Glydant ®
Merguard ® is Methyldibromo Glutaronitrile in Dipropylene Glycol

EXAMPLE 6

A series of different substrate sheets were evaluated for their usefulness for the present invention.

TABLE VI

| SUBSTRATE | PROPERTIES |
|---|---|
| 100% Rayon (PGI Spunlace Fabric) | too absorbent for printing; inks wicked providing poor print definition |
| 70% Rayon/30% Polyester (PGI Duralace Spunlace Fabric) | too absorbent for printing; inks wicked providing poor print definition |
| 50% Rayon/50% Polyester (PGI Sponge Fabric) | too absorbent for printing; inks wicked providing poor print definition |
| 50% Polypropylene/50% Rayon (PGI Thermal Bond Fabric) | too absorbent for printing; inks wicked providing poor print definition |
| 75% Polypropylene/25% Rayon (PGI Thermal Bond Fabric) | fabric was too coarse |
| 50% Cotton/50% Polyester (American Nonwovens Corp.) | poor surface to print on; fabric was too loose |
| 30% Pulp/70% Polyester (PGI Wet Form Fabric) | too stiff paper-like |
| 100% Polyester (Dupont Sontara 8100 ® Spunlace) | soft and printable surface |

From the above Table it can be seen that the substrate most useful to the present invention is that of polyester.

The foregoing description and examples illustrate selected embodiments of the present invention. In light thereof variations and modifications will be suggested to one skilled in the art, all of which are within the spirit and purview of this invention.

What is claimed is:

1. A cosmetic product comprising:

(i) a sealable container;

(ii) at least one absorbent pad with inked printing on at least one major surface thereof, the pad being enclosed within the container; and (iii) a cosmetic composition at least partially absorbed onto the absorbent pad.

2. The product according to claim 1 wherein the cosmetic composition comprises from 50 to 100% water by weight of the cosmetic composition.

3. The product according to claim 1 wherein the amount of water ranges from 80 to 99.9% by weight.

4. The product according to claim 1 wherein the pad is a non-woven polyester substrate.

5. The product according to claim 1 wherein the pad is printed with a cucumber slice cross section design.

6. The product according to claim 5 wherein the print is colored with yellow and blue dyes.

7. A method for treating eye areas to reduce or lessen conditions selected from the group consisting of puffiness, dark circles, redness and combinations thereof, comprising applying over the eye areas a pad printed with an inked design and impregnated with a cosmetic composition.

8. The method according to claim 7 wherein the cosmetic composition comprises from 50 to 100% water by weight of the composition.

9. The method according to claim 8 wherein the amount of water ranges from 80 to 99.9% by weight of the composition.

10. A product for use on the face comprising:

(i) a sealable container;

(ii) at least one absorbent sheet with inked printing on at least one major surface thereof, the sheet being enclosed within the container; and (iii) a cosmetic composition within the container and at least partially absorbed onto the absorbent sheet.

11. A process for producing a skincare product, the process comprising:

(i) placing a non-woven sheet under tension;

(ii) printing with ink from gravure plates a design onto the tensioned sheet;

(iii) cutting the printed sheets in register; and (iv) packaging the cut printed sheets along with a fluid cosmetic composition within a sealable container.

12. The process according to claim 11 wherein the gravure printing comprises applying a recessed image plate cylinder holding an image of the design to transfer same onto the tensioned sheet.

13. The process according to claim 12 wherein all elements within the design image are screened.

* * * * *

UNITED STATES PATENT AND TRADEMARK OFFICE
CERTIFICATE OF CORRECTION

PATENT NO. : 6,159,487
DATED : December 12, 2000
INVENTOR(S) : Znaiden et al.

It is certified that error appears in the above-indentified patent and that said Letters Patent is hereby corrected as shown below:

Change Title from "MOISTENED COSMETIC EYE TREATMENT FADS" TO

-- MOISTENED COSMETIC EYE TREATMENT PADS -- .

Signed and Sealed this

First Day of May, 2001

*Attest:*

NICHOLAS P. GODICI

*Attesting Officer*     Acting Director of the United States Patent and Trademark Office